US007001889B2

(12) United States Patent
Freehauf et al.

(10) Patent No.: US 7,001,889 B2
(45) Date of Patent: Feb. 21, 2006

(54) ANTHELMINTIC ORAL HOMOGENEOUS VETERINARY PASTES

(75) Inventors: Keith Freehauf, Stockton, NJ (US); Maryam Moaddeb, Collegeville, PA (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 10/177,822

(22) Filed: Jun. 21, 2002

(65) Prior Publication Data

US 2003/0236203 A1 Dec. 25, 2003

(51) Int. Cl.
| A01N 43/04 | (2006.01) |
| A01N 43/58 | (2006.01) |
| A61K 31/70 | (2006.01) |
| A61K 31/495 | (2006.01) |

(52) U.S. Cl. .......................... 514/29; 514/30; 514/248; 514/249; 514/250; 514/724; 424/94.1

(58) Field of Classification Search ................... 514/30, 514/29, 248, 249, 250, 724; 424/94.1

See application file for complete search history.

(56) References Cited

U.S. PATENT DOCUMENTS

| 3,502,661 | A | 3/1970 | Kasubick et al. |
| 3,950,360 | A | 4/1976 | Aoki et al. |
| 3,993,682 | A | 11/1976 | Kolling et al. |
| 4,001,441 | A | 1/1977 | Liepa |
| 4,032,655 | A | 6/1977 | Kolling et al. |
| 4,196,291 | A | 4/1980 | Seubert et al. |
| 4,197,307 | A | 4/1980 | Gallay et al. |
| 4,199,569 | A | 4/1980 | Chabalea et al. |
| 4,200,581 | A | 4/1980 | Fisher et al. |
| 4,310,519 | A | 1/1982 | Albers-Schonberg et al. |
| 4,427,663 | A | 1/1984 | Mrozik |
| 4,468,390 | A | 8/1984 | Kitano |
| 4,855,317 | A | 8/1989 | Gehret |
| 4,859,657 | A | 8/1989 | O'Sullivan et al. |
| 4,871,719 | A | 10/1989 | Maienfisch |
| 4,874,749 | A | 10/1989 | Mrozik |
| 4,920,148 | A | 4/1990 | Gehret |
| 4,963,582 | A | 10/1990 | Sato et al. |
| 4,973,711 | A | 11/1990 | Maienfisch |
| 4,978,677 | A | 12/1990 | Gehret |
| 5,055,596 | A | 10/1991 | Baker |
| 5,077,308 | A | 12/1991 | Blizzard |
| 5,089,490 | A | 2/1992 | Durckheimer |
| 5,824,653 | A | * 10/1998 | Beuvry et al. |
| 6,159,932 | A | 12/2000 | Mencke et al. |
| 6,165,987 | A | 12/2000 | Harvey |
| 6,207,179 | B1 | 3/2001 | Mihalik |
| 6,340,672 | B1 | 1/2002 | Mihalik |

FOREIGN PATENT DOCUMENTS

| EP | 0 001 688 | 5/1979 |
| EP | 0 001 689 | 5/1979 |
| EP | 0 021 758 | 1/1981 |
| EP | 214 738 | 3/1987 |
| WO | WO 94/10745 | 5/1994 |
| WO | WO 98/06407 | * 2/1998 |

OTHER PUBLICATIONS

Suleelman et al., "Photothermal Stability of Praziquantel", Oct. 2004, Scandi Pharmaceutical Journal, vol. 12, No. 4, pp. 157–162.

Chabala et al., J. Med. Chem. 1980, 23, pp. 1134–1136.

Egerton et al., Avemectins, New Family of Potent Anthelmintic Agents; Efficacy of the B1a Component—Antimicrobial Agents and Chemotherapy, Mar. 1979, pp. 372–378.

Egerton et al., Br. Vet. J. 1980, 136, pp. 88–97.

Obermeier et al., Arch Toxicol, 1977, 1977, vol. 38, pp. 149–161.

Davis et al., World Health Organisation 1979, 57 (5): pp. 767–771.

Thomas et al., Z. Parasitenk, 1977, 52, pp. 117–127.

Gönnert et al., Z. Parasitenk. 1977, 52, pp. 129–150.

Kobulej et al., Acta Veterinaria Academiae Scientiarum Hungaricae, 1976, vol. 26, 3, pp. 351–356.

Bylund et al., Journal of Helminthology, 1977, vol. 51, pp. 115–119.

Seubert et al., Experientia 1977, 33/8, pp. 1036–1037.

Roberson, Antinematodal Drugs and Anticestodal and Antitrematodal Drugs, Veterinary Pharmacology and Therapeutics, Iowa University Press 1977, Chapter 52, pp. 994–1051.

Roberson, Antinematodal Drugs and Anticestodal and Antitrematodal Drugs, Veterinary Pharmacology and Therapeutics, Iowa University Press 1977, Chapter 53, pp. 1052–1078.

(Continued)

Primary Examiner—James O. Wilson
Assistant Examiner—Traviss C. McIntosh, III
(74) Attorney, Agent, or Firm—Frommer Lawrence & Haug; Thomas J. Kowalski; Judy Jarecki-Black

(57) ABSTRACT

This invention provides for, inter alia, oral homogeneous veterinary pastes for the treating, controlling and preventing of endo- and ectoparasite infections in warm-blooded animals or birds, such as horses and household pets. This invention further provides for a process of preparing these veterinary pastes and for a method for increasing the bioavailability of the anthelmintic agent contained in the paste in the warm-blooded animal or bird. The inventive oral homogeneous anthelmintic pastes comprise a first anthelmintic agent, for example, prazequantel and/or pyrantel, and at least one marcrolide anthelmintic compound, a solvent, which dissolves both the first anthelmintic agent and second the macrolide anthelmintic compound, and a thickening agent. The inventive oral homogeneous pastes achieve a better bioavailability of the two active anthelmintic agents than when the two actives are in suspension and not dissolved

11 Claims, No Drawings

OTHER PUBLICATIONS

Theodorides, Antiparasitic Drugs, Parasitology for Veterinarians, WB Saunders Company 1980, Chapter 20.

Gibson, Past and Present Developments in Veterinary Anthelmintic Medication—Perspectives in the Control of Parasitic Disease in Animals in Europe, Royal College of Veterinary Surgeons 1977.

Parker, Fixed Dose Combinations and their Use in Veterinary Medicin, The Veterinary Bulletin 1976, vol. 46, Nr. 2, pp. 83–92.

Jacobs, Recent Developments in the Chemical Control of Helminths in Dogs and Cats, Royal College of Veterinary Surgeons 1977, pp. 45–52.

* cited by examiner

ANTHELMINTIC ORAL HOMOGENEOUS VETERINARY PASTES

BACKGROUND OF THE INVENTION

1. Field of the Invention

This invention provides for oral homogeneous veterinary pastes which are used in treating, controlling and preventing of endo- and ectoparasite infections in warm-blooded animals or birds, such as horses and household pets. This invention further provides for a process of preparing these veterinary pastes and for a method for increasing the bioavailability of the anthelmintic agents contained in the paste in the warm-blooded animal or bird. The inventive oral homogeneous anthelmintic pastes comprise a first anthelmintic agent, for example, praziquantel and/or pyrantel, and at least one macrolide anthelmintic compound, a solvent, which dissolves both the first anthelmintic agent and the macrolide anthelmintic compound, and a thickening agent. The inventive oral homogeneous pastes achieve a better bioavailability of the two active anthelmintic agents in the animal than when the two actives are in suspension and not dissolved.

2. Description of the Related Art

Therapeutic agents are administered to animals by a variety of routes. These routes include, for example, oral ingestion, topical application or parental administration. The particular route selected by the practitioner depends upon factors such as the physiochemical properties of the pharmaceutical or therapeutic agent, the condition of the host, and economic factors.

For example, one method of formulating a therapeutic agent for oral, topical, dermal or subdermal administration is to formulate the therapeutic agent as a paste or as and injectable formulation and reference is made to U.S. application Ser. No. 09/504,741, filed Feb. 16, 2000, now U.S. Pat. No. 6,787,342 entitled IMPROVED PASTE FORMULATIONS or to Ser. No. 09/346,905, filed Jul. 2, 1999, now U.S. Pat. No. 6,239,112; Ser. No. 09/112,690, filed Jul. 9, 1999 now U.S. Pat. No. 5,958,888 and Ser. No. 09/152,775, filed Sep. 14, 1998, now U.S. Pat. No. 6,174,540, entitled LONG ACTING INJECTABLE FORMULATIONS CONTAINING HYDROGENATED CASTOR OIL. The disclosure of these patent applications as well as the references cited therein and the references cited herein as well as the references cited in the references are expressly incorporated by reference. Other methods include placing the therapeutic agent in a solid or liquid matrix for oral delivery.

An important area in veterinary science in the control of endo- and ectoparasites in warm-blooded animals, such as equine animals and domestic pets. Infections of parasites, including cestodes and nematodes, commonly occur in animals such as horse, donkeys, mules, zebras, dogs, cats. Various classes anthelmintic agents have been developed in the art to control these infections; see, e.g., U.S. Pat. Nos. 3,993,682 and 4,032,655, which disclose phenylguanidines as anthelmintic agents. Further, the art recognizes that it is advantageous to administer combinations of two or more different classes of anthelmintic agents in order to improve the spectrum of activity; see, e.g., product disclosure for RM® Parasiticide-10, an anthelmintic paste comprising febantel and praziquantel.

Macrolide anthelmintic compounds are known in the art for treating endo- and ectoparasite infections in warm-blooded animals and birds. Compounds that belong to this class of agents include the avermectin and milbemycin series of compounds. These compounds are potent antiparasitic agents against a wide range of internal and external parasites. Avermectins and milbemycins share the same common 16-membered macrocyclic lactone ring; however, milbemycins do not possess the disaccharide substituent on the 13-position of the lactone ring. In addition to treating parasitic insects, such as flies, avermectins and milbemycins are used to treat endoparasites, e.g., round worm infections, in warm-blooded animals The avermectin and milbemycin series of compounds either are natural products or are semi-synthetic derivatives. The natural product avermectins are disclosed in U.S. Pat. No. 4,310,519 to Albers-Schonberg, et al., and the 22,23-dihydro avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, New York (1989). Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, N.J. (1996). Semi-synthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, and 4,920,148. All these documents are herein incorporated by reference.

Avermectins and milbemycins are ineffective against cestodes, such as tapeworms, which also are a common parasite in warm-blooded animals (see, U.S. Pat. No. 6,207, 179). Of particular importance in the industry is the treatment of equine tapeworms, in general, and *Anoplacephala perfoliata*, in particular (see, e.g., U.S. Pat. Nos. 6,207,179 or 5,824,653). In order to treat cestode (and trematode) infections in warm-blooded animals, it is know, to administer 2-acyl-4-oxo-pyrazino-isoquinoline derivatives to the animal (see, e.g., U.S. Pat. No. 4,001,441, herein incorporated by reference). A compound of this class that is often used to treat cestode and nematode infections is praziquantel, which has the following structure:

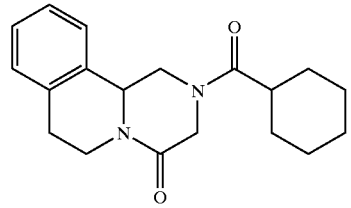

As mentioned above, often it is beneficial to administer a formulation that contains a combination of two or more anthelmintics, which possess different activity, in order to obtain a composition with a broad spectrum of activity. Further, the combination allows the user to administer one formulation instead of two or more different formulations to the animal. Formulations which administer a combination of two or more anthelmintics are know in the art. These formulations may be in the form of solutions, suspensions, pastes, drenches or pour-on formulations (see, e.g., U.S. Pat. No. 6,165,987 to Harvey or U.S. Pat. No. 6,340,672 to Mihalik). For example, U.S. Pat. No. 4,468,390 to Kitano and U.S. Pat. No. 5,824,653 to Beuvry et al. describe anthelmintic compositions for treating nematode and cestode infections in animals, such as horses, that comprise an avermectin or a milbemycin and an isoquinoline compounds, such as praziquantel, to the animal. In these formulations, the avermectin or milbemycin compound and the isoquinoline compound are not dissolved in a solvent, which is then dispersed in a semi-solid matrix. Similarly, U.S. Pat. No. 6,207,179 to Mihalik describes an anthelmintic paste formulations wherein the avermectin or milbemycin is dissolved in a non-aqueous liquid and pyrantel or morantel, compounds which are in the same class as praziquantel, but are said in the are to be far less effective as praziquantel, are suspended in the liquid. These prior patents do not describe a formulation wherein the both the praziquantel and the avermectin or milbemycin are dissolved in a solvent and then dispersed in a carrier matrix. U.S. Pat. No. 6,165,987 describes anthelmintic formulations containing praziquantel and at least one avermectin or milbemycin dissolved in an ester or ester-like compounds, such as glycerol formal, benzyl alcohol and N-methyl-2-pyrrolidone, which may be liquids, pastes or drenches; the amount of praziquantel administered to the animal is always at a dose of more that 2.0 mg per kg of body weight. U.S. Pat. No. 6,165,987 provides for pastes which require the presence of two solvents, one for the praziquantel and one for the macrolide compound.

SUMMARY OF THE INVENTION

This invention provides for oral homogeneous veterinary pastes for the treating, controlling and preventing of endo- and ectoparasite infections in warm-blooded animals, such as horses and household pests, and birds as well as to a process for preparing these formulations. The inventive oral anthelmintic pastes comprise a first anthelmintic agent, such as praziquantel and/or pyrantel, and, as second agent, at least one macrolide anthelmintic compound, such as an avermectin or milbemycin, dissolved in a solvent, which dissolves both the first anthelmintic compound and the macrolide anthelmintic compound, and a thickening agent. The inventive oral veterinary pastes provide for a more effective treatment of parasitic infections in non-human animals since the active ingredients do not interfere with each other, hence increasing the bioavailability in the animal, while still having the benefits of being administered by as a paste. Further, the inventive formulations provide for a formulation that exhibits good chemical and physical stability over the shelf-life of the product. Thus, the oral veterinary formulations of the invention exhibits the benefits of both a solution and a formulation that is a paste. Further, the present invention provides for a process for manufacturing the inventive formulations as well as a method to increase the bioavailability of the first anthelmintic agent and the macrolide anthelmintic compound in the warm-blooded animal or bird.

These and other embodiments are disclosed or are obvious form and encompassed by the following Detailed Description.

DETAILED DESCRIPTION

The present invention provides for an oral homogeneous anthelmintic veterinary paste, for the treating, controlling and preventing of endo-and ectoparasite infections in warm-blooded animal or birds, which comprises an anthelmintic agent, such a praziquantel, and/or pyrantel and, as a second agent, at least one macrolide anthelmintic agent, a solvent which dissolves both the first anthelmintic agent and the macrolide anthelmintic agent, and a thickening agent.

More specifically, this invention provides for an oral homogeneous veterinary paste consisting essentially of praziquantel and/or pyrantel and at least one macrolide anthelmintic compound, a solvent, which dissolves both the praziquantel and/or pyrantel and the macrolide anthelmintic compound, and at least one thickening agent. Preferred are oral homogeneous veterinary pastes consisting essentially of praziquantel and/or pyrantel and at least one macrolide anthelmintic compound, a solvent, which dissolves both the praziquantel and/or pyrantel and the macrolide anthelmintic compound, at least one thickening agent, and at least one viscosity modifier. Another embodiment of the invention is an oral veterinary composition consisting essentially of the inventive oral homogeneous veterinary pastes and an opacifier.

The inventive oral homogeneous veterinary pastes provide for the combination of at least two different anthelmintic agents, one of which is a macrolide anthelmintic compound. The classes of compounds encompassed by the first agent are well known to practitioners in this art. These compounds include, in addition to praziquantel and its related compounds, anthelmintic agents such as pyrantel (see, U.S. Pat. No. 3,502,661 for a description of pyrantel and its related compounds).

The invention provides for an oral homogeneous veterinary paste consisting essentially of praziquantel and/or pyrantel and at least one macrolide anthelmintic compound, a solvent, which dissolves both the praziquantel and/or pyrantel and the macrolide anthelmintic compound, at least one thickening agent, and at least one viscosity modifier. In a preferred embodiment, the macrolide anthelmintic compound is selected from the group consisting of doramectin, abamectin, moxidectin, selamectin and ivermectin; the solvent is glycerol formal, propylene glycol, n-methylpyrrolidone, or dimethyl sulfoxide; the thickening agent is selected from the group consisting of a cellulose, a starch, monothioglycerol, polymers or copolymers of polyvinylpyrrolidone, polymers and copolymers of (meth) acrylate, and a natural gum; and the viscosity modifier is selected from the group consisting of vegetable oils, or hydrogenated vegetable oils. In a preferred embodiment, the thickening agent is hydroxypropylcellulose, xanthum gum or hydroxyethyl starch and the viscosity modifier is hydrogenated castor oil, corn oil or olive oil.

The macrolide anthelmintic compounds contemplated in this invention are also well known to a practitioner of this are. These compounds include avermectins and milbemycins, some of which are discussed above. Non-limiting examples of compounds belonging to this class are represented by the following structure:

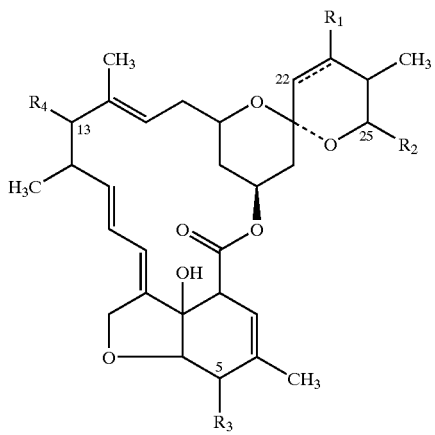

where the broken line indicates a single or a double bond at the 22,23-positions;

$R_1$ is hydrogen or hydroxy provided that $R_1$ is present only when the broken line indicates a single bond;

$R_2$ is alkyl of from 1 to 6 carbon atoms or alkenyl of from 3 to 6 carbon atoms or cycloalkyl of from 3 to 8 carbon atoms;

$R_3$ is hydroxy, methoxy or $=NOR_5$ where $R_5$ is hydrogen or lower alkyl; and $R_4$ is hydrogen, hydroxy or

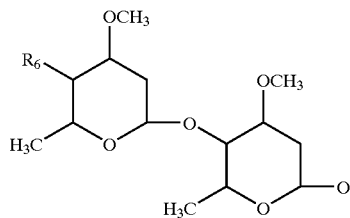

where $R_6$ is hydroxy, amino, mono-or di-lower alkylamino or lower alkanoylamino.

The preferred compounds are avermectin B1a/B1b (abamectin), 22,23-dihydro avermectin B1a/B1b (ivermectin) and the 4"-acetylamino-5-ketoximino derivative of avermectin B1a/B1b. Both abamectin and ivermectin are approved as broad spectrum antiparasitic agents. The structures of abamectin and ivermectin are as follows:

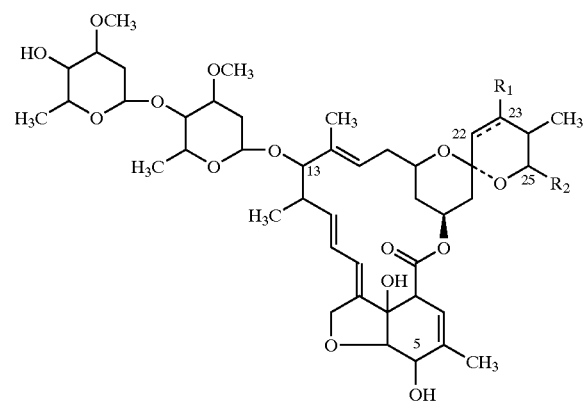

wherein for abamectin the broken line represents a double bond and $R_1$ is not present and for ivermectin the double bond represents a single bond and $R_1$ is hydrogen; and $R_2$ is isopropyl or sec-butyl.

The 4"-acetyl amino-5-ketoximino derivatives of avermectin B1a/B1b has the following structural formula:

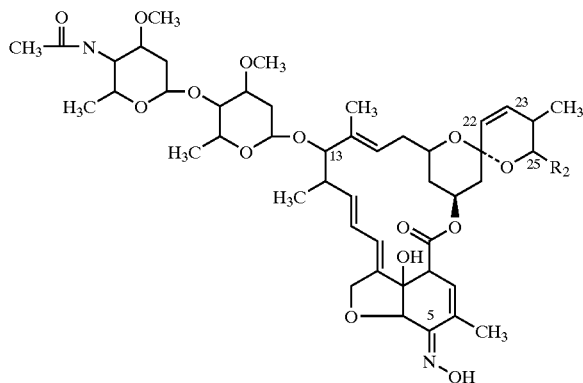

where $R_2$ is isopropyl or sec-butyl.

The avermectin products are generally prepared as a mixture of at least 80% of the compound where $R_2$ is sec-butyl and no more than 20% of the compound where $R_2$ is isopropyl.

Other preferred avermectins, include ememectin, epinomectin and doramectin. Doramectin is disclosed in U.S. Pat. No. 5,089,490 and EP 214 738. This compound has the following structure:

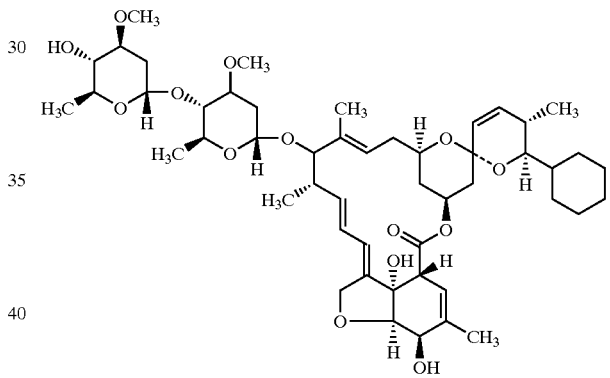

In the present formulations, ivermectin is especially preferred.

A representative structure for a milbemycin is that for milbemycin $\alpha_1$:

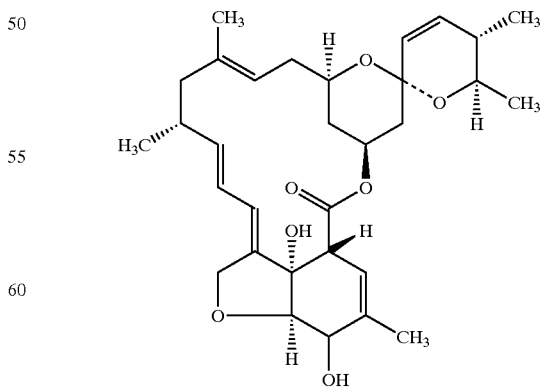

An especially preferred milbemycin is moxidectin, whose structure is as follows:

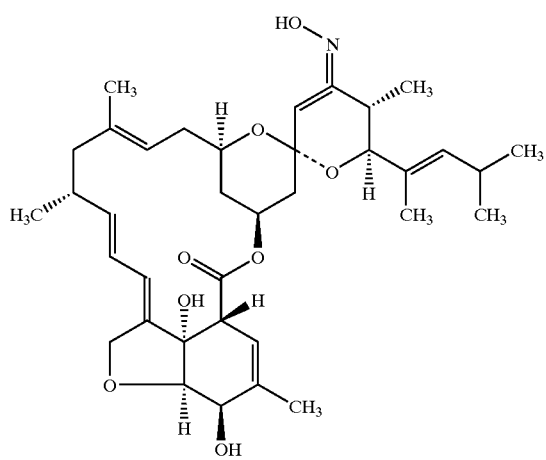

The compound is disclosed in U.S. Pat. No. 5,089,490.

The monosaccharide avermectin derivatives are also preferred especially where an oxime substitution is present on the 5-position of the lactone ring. Such compounds are described, for example, in EP 667,054. Selamectin is an especially preferred compound of this class of derivatives.

This application contemplates all pharmaceutically or veterinary acceptable acid or base salts forms of the anthelmintic compounds, where applicable. The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinary acceptable aliphatic, alicyclic and aromatic carboxylic acids, dicarboxylic acids tricarboxylic acids and fatty acids. Preferred acids are straight chain or branched, saturated or unsaturated $C_1$–$C_{20}$ aliphatic carboxylic acids, which are optionally substituted by halogen or by hydroxyl groups, or $C_6$–$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

The ester and amide derivatives of these compounds, where applicable, are also contemplated. Specific compounds which belong to this class of macrolide antiparasitic agents are well known to the practitioner of this art.

The solvents provided for in the inventive homogeneous pastes are those polar solvent that will dissolve both the first anthelmintic agent and the macrolide anthelmintic compound. These solvents include, for example, glycerol formal, 1-methylpyrrolidone (NMP), dimethyl sulfoxide (DMSO). Glycerol formal exists in two isomeric forms, the α,α'-form and the α,β-form. These forms are reproduced below:

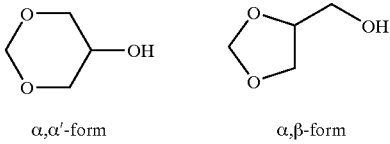

α,α'-form          α,β-form

The thickeners contemplated by this invention are well known to a practitioner of this art. Compounds which function as thickeners include, for example, celluloses, starches, natural gums, monothioglycerol, synthetic polymers, such as polymers and copolymers of polyvinylpyrrolidone or (meth)acrylates, etc. Especially preferred thickeners are hydroxypropylcellulose, xanthum gum and hydroxyethyl starch. Thickeners may be present in amounts of from about 3% to about 30%.

Opacifiers may be added to absorb and/or reflect certain light and/or energy of certain wavelengths and may thus enhance the stability of the formulations. Opacifiers include, for example, zinc oxide or titanium dioxide and may be present in amounts from about 0.5 to 2.5%. Titanium dioxide is especially preferred. These compounds are well known to practitioners of this art.

Additionally, the inventive formulations may contain other inert ingredients such as antioxidants, preservatives, or pH stabilizers. These compounds are well known in the formulation art. Antioxidant such as an alpha tocopheral, ascorbic acid, ascrobyl palmitate, fumeric acid, malic acid, sodium ascorbate, sodium metabisulfate, n-propyl gallate, BHA (butylated hydroxy anisole), BHT (butylated hydroxy toluene) monothioglycerol and the like, may be added to the present formulation. The antioxidants are generally added to the formulation in amounts of from about 0.01 to about 2.0%, based upon total weight of the formulation, with about 0.05 to about 1.0% being especially preferred. Preservatives, such as the parabens (methylparaben and/or propylparaben), are suitably used in the formulation in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Colorants may be added to the inventive formulations. Colorants contemplated by the present invention are those commonly known in the art. Specific colorants include, for example, dyes, an aluminum lake, caramel, colorant based upon iron oxide or a mixture of any of the foregoing. Especially preferred are organic dyes and titanium dioxide. Preferred ranges include from about 0.5% to about 25%.

Compounds which stabilize the pH of the formulation are also contemplates. Again, such compounds are well known to a practitioner in the art as well as how to use these compounds. Buffering systems include, for example, systems selected from the group consisting of acetic acid/acetate, malic acid/malate, citric acid/citrate, tataric acid/tartrate, lactic acid/lactate, phosphoric acid/phosphate, glycine/glycimate, tris, glutamic acid/glutamates and sodium carbonate. Preferred ranges for pH include from about 4 to about 6.5.

The inventive pastes may be administered to warm-blooded animals and birds. Warm-blooded animals include, for example, all ruminants, equines, canines and felines. Especially preferred are cattle sheep, pigs, dogs, cats, horses and the like. The amount of each of anthelmintic compounds is well known to a practitioner of this art. Preferred amounts of prazequantel include, for example, from about 0.5 mg/kg to about 7.5 mg/kg of animal body weight, with a range of about 0.5 mg/kg to about 2 mg/kg or 2.5 mg/kg of body weight being especially preferred. A most especially preferred amount is about 1.0 mg/kg of animal body weight. Preferred ranges for the anthelmintic macrolide compounds include, for example about 0.01 to about 200 mg/kg of animal body weight, with the ranges of about 0.1 to about 50 mg/kg and from about 1 to about 30 mg/kg being especially preferred.

The inventive oral homogeneous pastes may be prepared, for example, by a process which comprises:

dissolving the at least two different anthelmintic agents, e.g., praziquantel or pyrantel and macrolide anthelmintic compound or compounds, into the solvent; and adding the thickening agent or agents and stirring until a homogeneous paste is formed.

More preferred processes comprises:

dissolving the at least two different anthelmintic agents, e.g., praziquantel or pyrantel, and macrolide anthelmintic compound or compounds, and thickening agent or agents into the solvent and forming a thickened solution;

cooling the thickened solution to a temperature below about 35° C.

adding the viscosity modifier agent and stirring until a homogeneous paste is formed or dissolving the at least two different anthelmintic agents, e.g., praziquantel or pyrantel, and macrolide anthelmintic compound or compounds, the thickening agent or agents and least one compound selected from the group consisting of an antioxidant, a colorant, a pH stabilizer and/or a preservative into the solvent and forming a thickened solution;

cooling the solution to a temperature below about 35° C.; and adding the viscosity modifying agent or agents and stirring until a homogeneous paste is formed.

A preferred process to prepare the inventive oral veterinary compositions comprises:

dissolving the at least two different anthelmintic agents, e.g., parzequantel or pyrantel, and at least one macrolide anthelmintic compound or compounds and the thickening agent or agents into the solvent and forming a thickened solution;

adding the opacifier to the thickened solution and mixing until the opacifier is evenly dispersed;

cooling the thickened solution with the evenly dispersed opacifier to a temperature below about 35° C.;

adding the viscosity modifier and stirring until the oral veterinary composition is formed.

The inventive oral veterinary formulations may be used to treat a number of ecto- and endoparasite infections. The determining of a treatment protocol for an infection of a specific parasite or parasites would be well within the skill level of a practitioner of the veterinary art. This invention further provides for a method to increase the bioavailability of the at least two different anthelmintic agents in the animal.

EXAMPLES

A better understanding of the present invention and of its many advantages will be had from the following example, given by way of illustration.

An oral veterinary homogeneous paste, which had the following ingredients:

| INGREDIENTS | AMOUNT (% w/w) |
|---|---|
| Praziquantel | 7.75 |
| Ivermectin | 1.55 |
| Butylated hydroxyanisole (BHA) | 0.02 |
| Sunset Yellow (FD&C Yellow No. 6) | 0.04 |
| Titanium dioxide | 2.0 |
| Hydroxypropylcellulose (HPC) | 6.0 |
| Hydrogenated castor oil | 4.0 |
| Stabilized glycerol formal | QS AD 100 | was prepared by the following process:

1. Add some or all of the stabilized glycerol formal to a mixture followed by the addition of the praziquantel, ivermectin and BHA. The ingredients are mixed until they are dissolved in the stabilized glycerol formal.
2. Add sunset yellow to the solution and mix until dissolved.
3. Add titanium dioxide to the solution and mix until completely dispersed.
4. Add the remainder of glycerol formal, if necessary.
5. Add HPC to the solution and mix the solution until a homogeneous, viscous solution is obtained.
6. Cool the solution to a temperature below 35° C.
7. Once the solution is cooled to a temperature below 35° C., add the hydrogenated castor oil, while mixing, until all the hydrogenated castor oil is mixed into the solution; the temperature of the solution is maintained below 35° C.
8. Once the hydrogenated castor oil has been added, increase the agitation speed of the mixer while heating the mixture.
9. Mix until the product is a paste.

The above description of the invention is intended to be illustrative and not limiting. Various changes or modifications in the embodiment described may occur to those skilled in the art. These can be made without departing from the scope or spirit of the invention.

What is claimed is:

1. An oral veterinary paste consisting essentially of praziquantel, ivermectin, antioxidant, colorant, titanium dioxide, a cellulose, hydrogenated castor oil, and glycerol formal.

2. The oral veterinary paste according to claim 1 wherein the cellulose is hydroxypropylcellulose.

3. The oral veterinary paste of claim 1, wherein the cellulose is hydroxypropylcellulose and the glycerol formal is stabilized glycerol formal.

4. The oral veterinary paste of claim 1 which is produced by the process comprising:

(a) dissolving praziquantel, ivermectin, colorant, titanium dioxide, antioxidant and cellulose into glycerol formal to form a thickened solution;

(b) cooling the thickenened solution to a temperature below about 35° C.;

(c) adding hydrogenated castor oil to the thickened solution and stirring until a homogenous paste is formed, wherein the cellulose is hydroxypropyl cellulose and wherein the antioxidant is butylated hydroxyanisole, the opacifier is titanium dioxide and the colorant is sunset yellow (FD&C Yellow No. 6).

5. The oral veterinary paste according to claim 1, which is

| | |
|---|---|
| praziquantel | 7.75 % w/w |
| ivermectin | 1.55 % w/w |
| butylated hydroxyanisole | 0.02 % w/w |
| sunset yellow (FD&C Yellow No. 6) | 0.04 % w/w |
| titanium dioxide | 2.0 % w/w |
| hydroxypropylcellulose | 6.0 % w/w |
| hydrogenated castor oil | 4.0 % w/w |
| glycerol formal | QS AD 100. |

6. An oral veterinary paste comprising:

| | |
|---|---|
| praziquantel | 7.75 % w/w |
| ivermectin | 1.55 % w/w |
| hydroxypropylcellulose | 6.0 % w/w |
| hydrogenated castor oil | 4.0 % w/w |
| glycerol formal | QS AD 100 | and optionally, one or more compounds selected from the group consisting of an antioxidant, an opacifier and a colorant.

7. The oral veterinary paste of claim 6, wherein the antioxidant is butylated hydroxyanisole, the opacifier is titanium dioxide and the colorant is sunset yellow (FD&C Yellow No. 6).

8. A method for increasing the bioavailability of praziquantel and a macrolide anthelmintic compound in a warm-blooded animal which comprises administering the oral veterinary paste according to claim 1 to said warm-blooded animal.

9. The method of claim 8 wherein the warm-blooded animal is bird, cattle, sheep, pig, dog, cat or horse.

10. The method of claim 9 wherein the warm-blooded animal is a bird.

11. The method of claim 9 wherein the warm-blooded animal is a horse.

\* \* \* \* \*